(12) United States Patent  
Yoshimura et al.

(10) Patent No.: US 8,801,280 B2  
(45) Date of Patent: Aug. 12, 2014

(54) TEMPERATURE MEASURING METHOD USING TEMPERATURE-SENSITIVE MAGNETIC SUBSTANCE AND TEMPERATURE CONTROLLING METHOD

(75) Inventors: Noboru Yoshimura, Akita (JP); Kazutaka Mitobe, Akita (JP); Jun-ichi Ogawa, Akita (JP); Hajime Saito, Akita (JP)

(73) Assignee: Akita University, Akita-shi, Akita (JP)

( * ) Notice: Subject to any disclaimer, the term of this patent is extended or adjusted under 35 U.S.C. 154(b) by 1069 days.

(21) Appl. No.: 12/812,131

(22) PCT Filed: Jan. 9, 2009

(86) PCT No.: PCT/JP2009/050183  
§ 371 (c)(1),  
(2), (4) Date: Jul. 8, 2010

(87) PCT Pub. No.: WO2009/088062  
PCT Pub. Date: Jul. 16, 2009

(65) Prior Publication Data  
US 2010/0276501 A1    Nov. 4, 2010

(30) Foreign Application Priority Data

Jan. 10, 2008  (JP) ................................. 2008-003608  
Jun. 23, 2008  (JP) ................................. 2008-163226

(51) Int. Cl.  
*G01K 7/00*  (2006.01)  
*G01K 7/36*  (2006.01)

(52) U.S. Cl.  
USPC ........................................ 374/163; 374/100

(58) Field of Classification Search  
CPC ....... G01K 7/00; G01K 7/36; G01K 2217/00; G01K 374/163

USPC .......................................................... 374/163  
See application file for complete search history.

(56) References Cited

FOREIGN PATENT DOCUMENTS

| | | | | |
|---|---|---|---|---|
| CN | 2674449 | Y | * | 1/2005 |
| CN | 1900602 | A | * | 1/2007 |
| JP | 55-160720 | A | | 12/1980 |
| JP | 60-222030 | A | | 6/1985 |
| JP | 63-004986 | Y2 | | 10/1988 |
| JP | 03-256086 | A | | 11/1991 |
| JP | 08-286542 | A | | 11/1996 |
| JP | 3333875 | B2 | | 10/2002 |
| JP | 2007-078825 | A | | 3/2007 |
| JP | 2007078825 | A | * | 3/2007 |
| JP | 2011027527 | A | * | 2/2011 |

OTHER PUBLICATIONS

Office Action dated Dec. 1, 2011 in regards to CN200980101841.9  
International Search Report: PCT/JP2009/050183.

* cited by examiner

*Primary Examiner* — Lisa Caputo  
*Assistant Examiner* — Jamel Williams  
(74) *Attorney, Agent, or Firm* — Ladas & Parry LLP

(57) ABSTRACT

A temperature measuring method using a temperature probe in which a temperature-sensitive magnetic substance having an arbitrary Curie point is arranged in a portion to be measured. A magnetic field is generated from a magnetic field generation source disposed at a position away from the portion to be measured. A change of the magnetic flux vector of the magnetic field depending on the temperature of the temperature-sensitive magnetic substance is detected by a magnetic sensor to measure the temperature of the portion to be measured, thereby the temperature of the portion to be measured can be wirelessly measured from the position away from the portion to be measured and the reduction in size can be easy.

16 Claims, 6 Drawing Sheets

TEMPERATURE MEASURING METHOD USING TEMPERATURE-SENSITIVE MAGNETIC SUBSTANCE AND TEMPERATURE CONTROLLING METHOD

TECHNICAL FIELD

The present invention relates to a temperature measuring method which can measure a temperature of a portion to be measured from a position away from the portion to be measured by detecting the change of the magnetic flux vector of a magnetic field changed depending on the temperature of a temperature-sensitive magnetic substance, a temperature controlling method using the temperature measuring method, and a system for use in those methods.

BACKGROUND ART

As one means for treating malignant tumors, there is thermotherapy using microwaves or high-frequency electric currents as an energy source. When performing the thermotherapy, it is necessary to make sure that the temperature of an affected part reaches the target temperature. As a temperature measuring technique, there is a thermal camera using infrared rays. However, this is mainly used only for measuring a surface temperature and cannot measure a temperature in a living body through which no infrared rays can transmit. Therefore, to measure the temperature of an affected part, it is considered that a temperature probe such as a thermistor or a thermocouple is invasively inserted into a body. However, in such method, there are a problem of paining patients and a hygienic problem of causing infectious disease.

To solve such problems, a technique which can wirelessly measure the temperature of a portion to be measured from a position away from the portion to be measured has been considered and disclosed. For instance, Patent Document 1 discloses a temperature measuring method in which a temperature measuring element having a permanent magnet and a plurality of temperature-sensitive magnetic substances covering the periphery of the permanent magnet and having different Curie points is arranged in a portion to be measured, a leakage magnetic flux leaked from the temperature measuring element depending on temperature is detected by a magnetic sensor arranged in the position away from the temperature measuring element, and the temperature of the portion to be measured is measured according to the output.

Patent Document 1: Japanese Patent No. 3333875

DISCLOSURE OF THE INVENTION

Problems to be Solved by the Invention

In the temperature measuring method disclosed in Patent Document 1, because the temperature measuring element (temperature probe) arranged in the portion to be measured has a multilayer structure including a permanent magnet and a plurality of temperature-sensitive magnetic substances, there remains the problem that even when the layers become thinner, the reduction of the size of the temperature measuring element is limited.

Accordingly, an object of the present invention is to provide a temperature measuring method using a temperature probe which can wirelessly measure the temperature of a portion to be measured from the position away from the portion to be measured and can be easily reduced in size.

Means for Solving the Problems

To address the above object, a first invention provides a temperature measuring method, comprising the steps of: arranging in a portion to be measured a temperature-sensitive magnetic substance having an arbitrary Curie point; generating a magnetic field from a magnetic field generation source disposed at a position away from the portion to be measured; and detecting a change of the magnetic flux vector of the magnetic field depending on the temperature of the temperature-sensitive magnetic substance by a magnetic sensor, whereby the temperature of the portion to be measured is measured.

Such temperature measuring method of the present invention is applicable to almost any kind of thermotherapy, which can be incorporated into an existing thermotherapy device using induction heating or microwaves. In addition, because a tumor temperature can be non-invasively monitored, any load on and infectious risk to patients can be reduced. Further, because the present invention is applicable to a non-magnetic substance target, a temperature in an object which has been required to be wiredly measured using a thermistor or a thermocouple can be wirelessly measured.

In the present invention, the "temperature-sensitive magnetic substance" means a magnetic substance made of magnetic material which can arbitrarily set the Curie point according to a change of a composition ratio, an addition of an additive, and a thermal treatment. Specific examples of the magnetic material which can be used in the present invention can include an Ni—Zn ferrite and an Mn—Cu—Zn ferrite. When using the temperature measuring method of the present invention for measuring the temperature of an affected part in performing thermotherapy, it is preferable to select a magnetic material which can set the Curie point at about 43° C. Specific examples of such magnetic material can include an Ni—Zn ferrite and an Mn—Cu—Zn ferrite. The "magnetic field generation source" is not particularly limited as long as it can generate a magnetic field. Specific examples thereof can include a coil, a superconductive coil, and a permanent magnet. The "position away from the portion to be measured" is preferably 20 cm or less, more preferably 10 cm or less, and most preferably 5 cm or less. The "magnetic sensor" is not particularly limited as long as it can detect the change of the magnetic flux vector of a magnetic field. Specific examples thereof can include a coil, a hall device, a magnetoresistance effect device, a flux gate sensor, a Faraday element, and a superconducting quantum interference device.

In the temperature measuring method of the first invention, a plurality of temperature-sensitive magnetic substances having arbitrary different Curie points can be arranged in a portion to be measured. In such a form, a plurality of target temperatures can be detected. In other words, the temperature measuring method of the present invention is a general-purpose non-contact temperature measuring technique which is not limited to the utilization in the thermotherapy and enables continuous temperature measurement using a plurality of temperature-sensitive magnetic substances respectively having arbitrary different Curie points.

In the temperature measuring method of the first invention, the magnetic field generation source is preferably a coil which flows an alternating current and the magnetic sensor is also preferably a coil. In such a form, it is possible to improve the durability of the system and possible to reduce the cost. Moreover, the cross-axis effect caused in a semiconductor device can be completely removed.

In the temperature measuring method of the first invention, the temperature-sensitive magnetic substance used as a temperature probe can be particulate for use. As used herein, the term "particulates" means microparticles having an average diameter of about 150 μm or less. By processing the temperature-sensitive magnetic substance into microparticles, the temperature-sensitive magnetic substance particulates can be dispersed into a liquid such as a physiological salt solution and can be injected into a living body using an injection needle. Moreover, by processing the temperature-sensitive magnetic substance into microparticles, the temperature-sensitive magnetic substance particulates reduce the thermal capacity of the temperature-sensitive magnetic substance. Accordingly, the temperature near the Curie point can be detected at high sensitivity.

In the temperature measuring method of the first aspect of the invention, an exothermic material which is easily inductively heated is preferably used together with the magnetic material as the temperature-sensitive magnetic substance. As used herein, the term "exothermic material which is easily inductively heated" specifically can include metals such as Fe, Au, Ti, and Pt, and an alloy which has one or more of these metals as the main component. When using the "exothermic material which is easily inductively heated" for the thermotherapy, in consideration of the influence on a human body, metals such as Au and Ti and an alloy including those metals are preferably selected. The exothermic material which is easily inductively heated is used together with the magnetic material for the temperature-sensitive magnetic substance, so that the thermotherapy at a low magnetic flux density can be attained and the power source equipment can be downsized.

In the temperature measuring method of the first aspect of the invention, preferably, the relative positions and postures of the magnetic sensor and the magnetic field generation source are adjusted and fixed so that the output of the magnetic sensor is a minimum value ($V_{min}$); the temperature-sensitive magnetic substance is arranged in the portion to be measured, and the relative positions and postures of the magnetic sensor, the magnetic field generation source, and the temperature-sensitive magnetic substance are adjusted and fixed so that the output of the magnetic sensor is a maximum value ($V_{max}$); and the output (V) of the magnetic sensor when the temperature of the portion to be measured reaches the target temperature is calculated from the following calculation equation:

calculation equation: $V=(V_{max}-V_{min}) \times k + V_{min}$
(wherein, $k$ is a constant of $0<k<1$).

Using such a method, as described later, even when the amount and the arranged position of the temperature-sensitive magnetic substance in an object to be measured are not clearly predetermined, whether or not the temperature of the portion to be measured reaches the target temperature can be detected.

A second aspect of the invention provides a temperature measuring system comprising: a temperature-sensitive magnetic substance arranged in a portion to be measured and having an arbitrary Curie point; and a detecting portion which generates a magnetic field in a position away from the portion to be measured and detects a change of the magnetic flux vector of the magnetic field depending on the temperature of the temperature-sensitive magnetic substance.

In the temperature measuring system of the second aspect of the invention, the detecting portion can have a magnetic field generation source which generates a magnetic field at a position away from the portion to be measured, and a magnetic sensor which detects the change of the magnetic flux vector of the magnetic field depending on the temperature of the temperature-sensitive magnetic substance; and the detecting portion preferably has a lock-in amplifier.

A third aspect of the invention provides a temperature controlling method, wherein a temperature-sensitive magnetic substance having an arbitrary Curie point is arranged in a portion to be measured and the portion to be measured is heated by a heating device, wherein a magnetic field is generated from a magnetic field generation source disposed at a position away from the portion to be measured, a change of the magnetic flux vector of the magnetic field depending on the temperature of the temperature-sensitive magnetic substance is detected by a magnetic sensor, wherein the heating device is controlled according to a detection signal from the magnetic sensor.

In the temperature controlling method of the third aspect of the invention, the magnetic field generation source can serve as the heating device. The temperature-sensitive magnetic substance or an exothermic material which is easily inductively heated and is used together with the temperature-sensitive magnetic substance is inductively heated by a magnetic field generated by the magnetic field generation source, so that the portion to be measured can be heated.

A fourth aspect of the invention provides a temperature controlling system including: a temperature-sensitive magnetic substance arranged in a portion to be measured and having an arbitrary Curie point; a detecting portion which generates a magnetic field in a position away from the portion to be measured and detects the change of the magnetic flux vector of the magnetic field depending on the temperature of the temperature-sensitive magnetic substance; a heating portion which heats the portion to be measured; and a controlling portion having a computer which controls the heating portion according to a detection signal obtained from the detecting portion.

In the temperature controlling system of the fourth aspect of the invention, the detecting portion has a magnetic field generation source which generates a magnetic field in a position away from the portion to be measured, and the magnetic field generation source can serve as the heating portion by inductively heating the temperature-sensitive magnetic substance.

Effect of the Invention

According to the temperature measuring method of the first aspect of the invention, the temperature of the portion to be measured can be wirelessly measured from a position away from the portion to be measured. By using the temperature-sensitive magnetic substance as the temperature probe, the temperature probe can be easily downsized. According to the second aspect of the invention, the temperature measuring system which can wirelessly measure the temperature of the portion to be measured from the position away from the portion to be measured can be provided. According to the third aspect of the invention, the temperature controlling method which can control the temperature of the portion to be measured by wirelessly measuring the temperature of the portion to be measured from a position away from the portion to be measured can be provided. According to the fourth aspect of the invention, the temperature controlling system which can control the temperature of the portion to be measured by wirelessly measuring the temperature of the portion to be measured from the position away from the portion to be measured can be provided.

DESCRIPTION OF REFERENCE NUMERALS

Figure 1A:
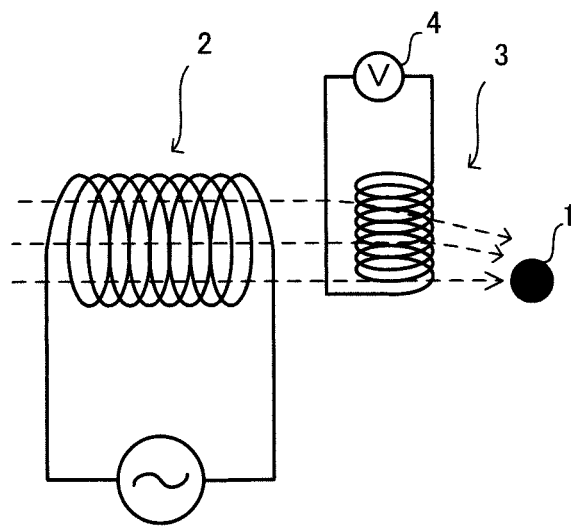
FIGS. 1A and 1B are diagrams schematically showing the principle of a temperature measuring method of the present invention.

1 Temperature-sensitive magnetic substance
2 Driving coil (magnetic field generation source)
3 Pickup coil (magnetic sensor)
4 Voltmeter
5 Oscillator
6 Lock-in amplifier
7 Power amplifier
8 High-frequency alternating-current power source
9 Resistor
10 Temperature measuring system
15 Detecting portion
20 Heating portion
21 Heating power source
22 Heating device
30 Controlling portion
31 Computer for controlling measurement
40 Object to be measured (i.e. human body)
100 Temperature controlling system

BEST MODE FOR CARRYING OUT THE INVENTION

<Temperature Measuring Method>

A temperature measuring method of the present invention will be described below with reference to the drawings.

Figure 1B:
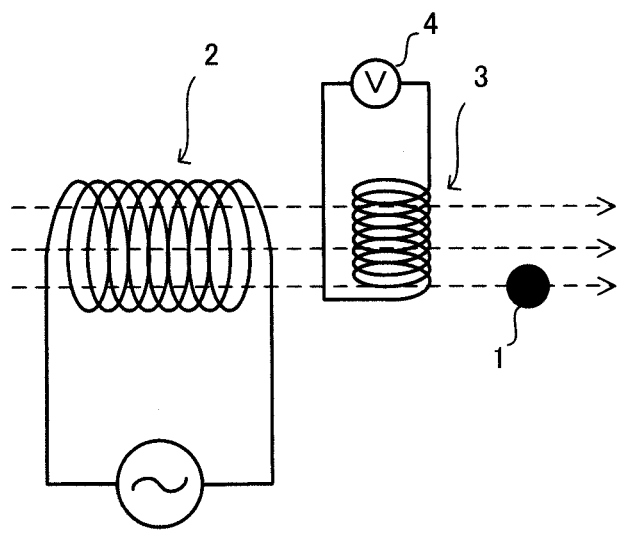

FIGS. 1A and 1B are diagrams schematically showing the principle of a temperature measuring method of the present invention. The dashed arrows in the drawing indicate the magnetic flux lines of an alternating-current magnetic field. FIG. 1A shows the state that the temperature of a temperature-sensitive magnetic substance 1 is less than the Curie point, and FIG. 1B shows the state that the temperature of the temperature-sensitive magnetic substance 1 is the Curie point or more.

The temperature-sensitive magnetic substance 1 is a magnetic substance made of magnetic material set at an arbitrary target temperature. A magnetic field generation source 2 is a coil which generates an alternating-current magnetic field by flowing an alternating current (hereinafter, referred to as a "driving coil".). A magnetic sensor 3 is a coil which detects a change of the magnetic flux vector of an alternating-current magnetic field generated from the driving coil 2 (hereinafter, referred to as a "pickup coil".). The driving coil 2 and the pickup coil 3 are arranged so that their axial directions are orthogonal to each other.

When the temperature of the temperature-sensitive magnetic substance 1 is lower than the Curie point of the temperature-sensitive magnetic substance 1, the temperature-sensitive magnetic substance 1 has high magnetic permeability. So, as shown in FIG. 1A, the magnetic flux of an alternating-current magnetic field generated from the driving coil 2 is attracted to the temperature-sensitive magnetic substance 1 and the magnetic flux vector is bent. At this time, an induced electromotive force in proportion to the change of the orthogonal component of the magnetic flux vector is generated in the pickup coil 3 arranged between the temperature-sensitive magnetic substance 1 and the driving coil 2, thereby generating a potential.

When the temperature of the temperature-sensitive magnetic substance 1 is the Curie point of the temperature-sensitive magnetic substance 1 or more, the magnetic properties of the temperature-sensitive magnetic substance 1 are about the same as air. Therefore, as shown in FIG. 1B, the magnetic flux of the alternating-current magnetic field generated from the driving coil 2 travels in a substantially straight line without being attracted to the temperature-sensitive magnetic substance 1, and the magnetic flux vector and the axis of the pickup coil 3 are substantially orthogonal to each other. Thus, an induced electromotive force generated in the pickup coil 3 is reduced as compared with the case where the temperature of the temperature-sensitive magnetic substance 1 is less than the Curie point.

When the temperature of the temperature-sensitive magnetic substance 1 is increased, an induced electromotive force generated in the pickup coil 3 near the Curie point is abruptly changed. That is, by disposing the temperature-sensitive magnetic substance 1 in a portion to be measured to generate an alternating-current magnetic field in a position away from the temperature-sensitive magnetic substance 1; and then, by detecting the change of the magnetic flux vector of the alternating-current magnetic field depending on the temperature of the temperature-sensitive magnetic substance 1, it is possible to check that the temperature of the periphery (portion to be measured) of the temperature-sensitive magnetic substance 1 is the arbitrary temperature (the Curie point of the temperature-sensitive magnetic substance 1) or more. According to the temperature measuring method of the present invention, the temperature of the portion to be measured can be wirelessly measured from the position away from the portion to be measured.

Because the temperature measuring method of the present invention is applicable to almost any kind of thermotherapy, it can be incorporated into an existing thermotherapy device using induction heating or microwaves. According to the temperature measuring method of the present invention, a tumor temperature can be monitored in a non-contact and non-invasive manner. Therefore, any load on and infectious risk to patients can be reduced.

When the temperature measuring method of the present invention is applied to thermotherapy, the exothermic material which is easily inductively heated is preferably used together with the temperature-sensitive magnetic substance. In such form, the heat generation efficiency of thermotherapy which applies a high-frequency magnetic field from the outside of a body can be improved and therapy at a low magnetic flux density using a low-output power source is enabled, thereby the power source equipment can be downsized.

The position which can be measured by the temperature measuring method of the present invention is not limited to the inside of a living body; the present invention is applicable to any non-magnetic substance object. The method can be applicable to solid, liquid, and gas as long as the material can transmit a magnetic field. A temperature in an object which has been conventionally required to be wiredly measured using a thermistor or a thermocouple can be measured wirelessly.

In the description of the principle of the temperature measuring method of the present invention with reference to FIGS. 1A and 1B, there illustrates the form in which the pickup coil 3 is arranged between the driving coil 2 and the temperature-sensitive magnetic substance 1 so that the axial directions of the driving coil 2 and the pickup coil 3 are orthogonal to each other. The present invention is not limited to such a form. The relative positions of the temperature-sensitive magnetic substance 1, the driving coil 2, and the pickup coil 3 need to be fixed at the time of temperature measurement, and the temperature-sensitive magnetic substance 1, the driving coil 2, and the pickup coil 3 may be arranged so as to be close to each other to the extent that they are influenced on each other.

In the description of the principle of the temperature measuring method of the present invention with reference to FIGS. 1A and 1B, the example using one temperature-sensitive magnetic substance has been described. However, the present invention is not limited to such form; a plurality of temperature-sensitive magnetic substances can be used. So, by disposing a plurality of temperature-sensitive magnetic substances respectively having different Curie points in the portion to be measured under the conditions that the relative position relation between the temperature-sensitive magnetic substances, the magnetic sensor, and the magnetic field generation source is fixed, a plurality of target temperatures can be detected. The temperature measuring method of the present invention is a general-purpose non-contact temperature measuring technique which is not limited to the utilization in the thermotherapy and enables continuous temperature measurement using a plurality of temperature-sensitive magnetic substances having arbitrary different Curie points.

In the temperature measuring method of the present invention, the temperature-sensitive magnetic substance is used as a temperature probe and the temperature-sensitive magnetic substance can be particulates. For example, when the temperature-sensitive magnetic substance (temperature probe) is processed into particulates having an average particle size of about 150 μm or less, it is possible to disperse it into a liquid such as a physiological salt solution and then inject into a living body using an injection needle for use. Moreover, by processing the temperature-sensitive magnetic substance into particulates, the thermal capacity of the temperature-sensitive magnetic substance decreases. So, the temperature near the Curie point can be detected at high sensitivity. When the temperature-sensitive magnetic substance is arranged in a living body, the size of the temperature-sensitive magnetic substance is preferably large to some extent in order that the temperature-sensitive magnetic substance cannot move through a lymphatic vessel.

As other methods of arranging the temperature-sensitive magnetic substance in the portion to be measured in a living body, a method of using an injector for solid medicine is considered. When using this method, the particle size of the temperature-sensitive magnetic substance is preferably 2 mm or less.

As other methods of arranging the temperature-sensitive magnetic substance in the portion to be measured, a method of arranging the encapsulated temperature-sensitive magnetic substance in the portion to be measured is considered. The capsule having a particle size of 2 mm or less can be arranged in a living body using the injector. By using the capsule, the temperature-sensitive magnetic substance encapsulated together with the exothermic material which is easily inductively heated can be easily arranged in the portion to be measured. When the temperature-sensitive magnetic substance and so on are arranged in a living body using a capsule, an effect of preventing the temperature-sensitive magnetic substance from being dispersed in a living body and an effect which is capable of using the temperature-sensitive magnetic substance even when the temperature-sensitive magnetic substance negatively affects the living body while separating it from the living body. When the capsule is arranged in a living body, the material of the capsule is not particularly limited as long as the material does not negatively affect the living body. For instance, silicone, resin, and titanium can be used.

Figure 2:
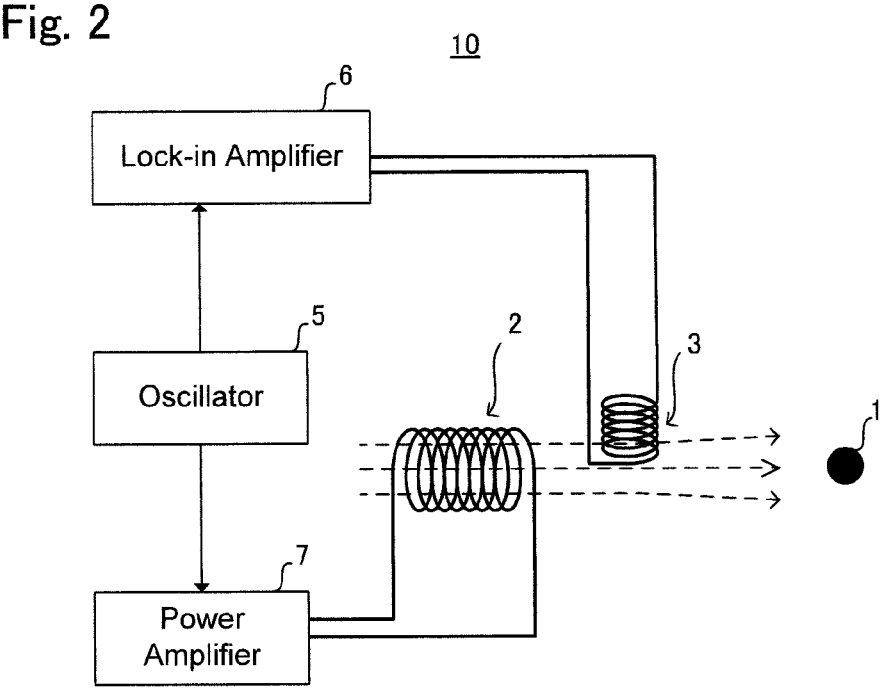
FIG. 2 is a diagram schematically showing an example of a temperature measuring system of the invention.

FIG. 2 is a diagram schematically showing an example of a temperature measuring system of the present invention. The three dashed arrows indicate the magnetic flux lines of an alternating-current magnetic field generated from the driving coil 2. In FIG. 2, parts having the same configuration as those of FIGS. 1A and 1B are indicated by the same reference numerals as those numerals used in FIGS. 1A and 1B.

As shown in FIG. 2, a temperature measuring system 10 has the temperature-sensitive magnetic substance 1, the driving coil 2, the pickup coil 3, an oscillator 5, a lock-in amplifier 6, and a power amplifier 7.

The process for detecting the change of the magnetic flux vector of an alternating-current magnetic field generated from the driving coil 2 will be described as below.

When an electric signal is input from the oscillator 5 to the power amplifier 7 and an alternating current flows from the power amplifier 7 to the driving coil 2, an alternating-current magnetic field is generated from the driving coil 2. The alternating-current magnetic field is affected by the magnetic properties of the temperature-sensitive magnetic substance 1 located at an arbitrary distance from the driving coil 2. The magnetic properties of the temperature-sensitive magnetic substance 1 depend on the temperature of the temperature-sensitive magnetic substance 1, so that the alternating-current magnetic field generated by the driving coil 2 is affected by the temperature of the temperature-sensitive magnetic substance 1. When the temperature of the temperature-sensitive magnetic substance 1 is less than the Curie point, the magnetic flux vector of the alternating-current magnetic field generated by the driving coil 2 is bent. When the temperature of the temperature-sensitive magnetic substance 1 is the Curie point or more, the magnetic flux vector of the alternating-current magnetic field generated by the driving coil 2 travels in a substantially straight line between the driving coil 2 and the temperature-sensitive magnetic substance 1.

As described above, when the magnetic flux vector of an alternating-current magnetic field generated by the driving coil 2 is bent, an induced electromotive force is generated in the pickup coil 3; when the magnetic flux vector and the axis of the pickup coil 3 are substantially orthogonal to each other, an induced electromotive force generated in the pickup coil 3 is reduced as compared with the case where the magnetic flux vector is bent. That is, when the temperature of the temperature-sensitive magnetic substance 1 is the Curie point or more, an induced electromotive force generated in the pickup coil 3 is reduced as compared with the case where the temperature of the temperature-sensitive magnetic substance 1 is less than the Curie point. Therefore, by detecting an induced electromotive force generated in the pickup coil 3 disposed between the driving coil 2 and the temperature-sensitive magnetic substance 1, it is possible to make sure whether or not the temperature of the portion to be measured reaches the target temperature (the arbitrarily set Curie point of the temperature-sensitive magnetic substance). However, when the driving coil 2 and the temperature-sensitive magnetic substance 1 are spaced from each other, the amount of change in the magnetic flux vector is reduced, so that an induced electromotive force generated in the pickup coil 3 is hard to be detected. In the temperature measuring system 10, an electric signal is input from the oscillator 5 to the power amplifier 7, an electric signal (reference signal) is also input from the oscillator 5 to the lock-in amplifier 6 connected to the pickup coil 3, and the induced electromotive force generated in the pickup coil 3 is synchronously detected by the lock-in amplifier 6 so as to reduce magnetic field noise in the periphery and to improve the detection sensitivity.

A method of detecting whether or not the temperature of the portion to be measured reaches the target temperature even when the dosage and arranged position of the temperature-sensitive magnetic substance 1 in an object to be measured are not clear will be described below with reference to FIGS. 3 to 5.

Figure 3:
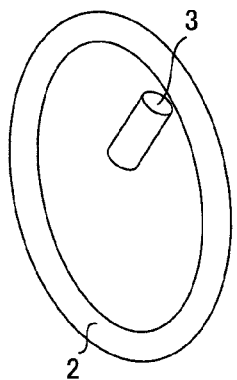
FIG. 3 is a diagram schematically showing an example of the arrangement of a driving coil and a pickup coil.

FIG. 3 is a diagram schematically showing an example of the arrangement of the driving coil 2 and the pickup coil 3. FIG. 4 is a diagram schematically showing an example of an embodiment of the temperature measuring method of the present invention. FIG. 5 is a diagram showing the relation between the temperature of the temperature-sensitive magnetic substance 1 in an object to be measured and the output voltage of the pickup coil 3. In FIGS. 3 and 4, elements having the same configuration as those of FIGS. 1A, 1B, and 2 are indicated by the same reference numerals as those used in FIGS. 1A, 1B, and 2.

Figure 4:
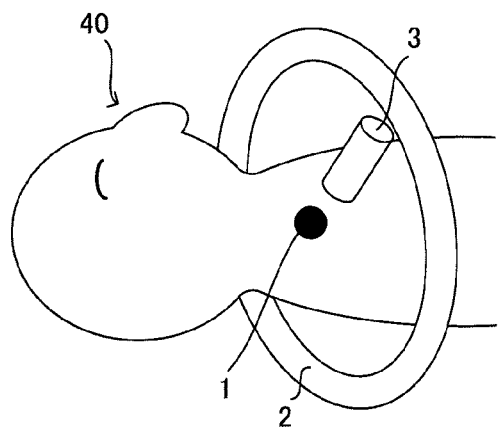
FIG. 4 is a diagram schematically showing an example of an embodiment of the temperature measuring method of the invention.
Figure 5:
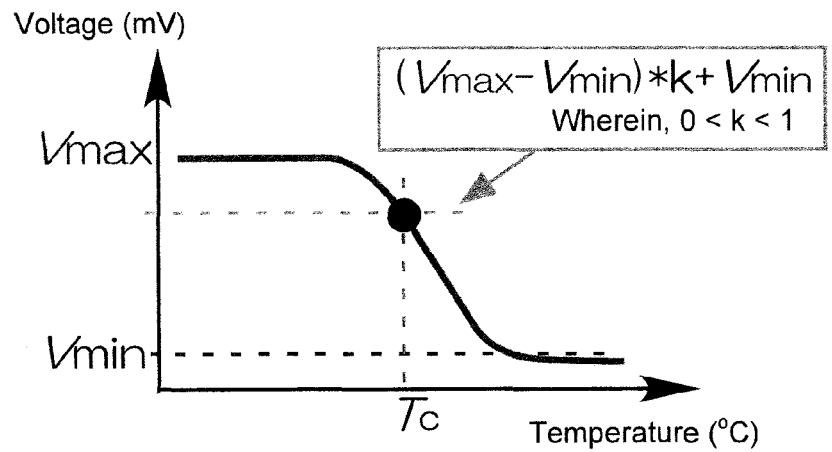
FIG. 5 is a diagram showing the relation between the temperature of a temperature-sensitive magnetic substance in an object to be measured and the output voltage of the pickup coil.

As shown in FIG. 3, the relative positions and the relative postures of the driving coil 2 and the pickup coil 3 are adjusted and fixed so that the output voltage of the pickup coil 3 is minimum without an object to be measured 40 (see FIG. 4). The output voltage of the pickup coil 3 in this posture is defined as $V_{min}$. In the following measurement, the relative positions and postures of the driving coil 2 and the pickup coil 3 are not changed. Therefore, when there is a magnetic substance or metal in the periphery, the magnetic flux vector generated from the driving coil 2 is changed and the voltage value of the pickup coil 3 becomes larger than $V_{min}$.

As shown in FIG. 4, the temperature-sensitive magnetic substance 1 is arranged in the position to be measured of the object to be measured (e.g., human body) 40 and the position and posture of the object to be measured 40 in which the temperature-sensitive magnetic substance 1 is arranged are adjusted so that the output voltage of the pickup coil 3 is maximum. The output voltage of the pickup coil 3 in this posture is defined as $V_{max}$. By this operation, it is possible to detect that the temperature of the portion to be measured reaches the target temperature without depending on the position, posture, and mass of the temperature-sensitive magnetic substance 1 arranged in the object to be measured 40.

When the temperature in the periphery of the temperature-sensitive magnetic substance 1 is increased, the temperature-sensitive magnetic substance 1 is also heated. Eventually, the temperature of the temperature-sensitive magnetic substance 1 reaches the Curie point and the magnetic permeability of the temperature-sensitive magnetic substance 1 decreases. As a result, the amount of change of the magnetic flux vector is reduced, so that the output of the pickup coil 3 is close to $V_{min}$.

An example of a measurement algorithm which detects that the temperature of the portion to be measured reaches the target temperature by the device shown in FIG. 4 will be shown below. By using the $V_{min}$ and $V_{max}$, as shown in FIG. 5, the voltage value (V) of the pickup coil 3 when the temperature of the temperature-sensitive magnetic substance 1 reaches the Curie point (Tc) can be determined from the following calculation equation using an arbitrary constant k. The voltage value of the pickup coil 3 is measured, so that the temperature of the portion to be measured reaches the target temperature.

Calculation equation: $V=(V_{max}-V_{min}) \times k + V_{min}$

Here, the constant k (0<k<1) is a value determined by the thermal capacity of the portion to be measured (and the periphery thereof), the amount of the temperature-sensitive magnetic substance 1, and the relative positions and postures of the driving coil 2 and the pickup coil 3; it can also be experimentally calculated. When the voltage value of the pickup coil 3 in the heating process is temporally differentiated in real time, it can be detected that the temperature of the portion to be measured reaches the target temperature from the maximum value of the amount of change of the voltage value of the pickup coil 3.

By using other magnetic material or metal material together with the temperature-sensitive magnetic substance 1, in the state that the heat generation efficiency by induction heating is improved, it can be detected that the temperature of the portion to be measured reaches the target temperature. In this case, even when a bias is caused in the voltage value of the pickup coil 3 because the magnetic flux vector is bent by other material used concurrently and the temperature of the portion to be measured reaches the target temperature and reaches the Curie point of the temperature-sensitive magnetic substance 1, the voltage value of the pickup coil 3 is not lowered to $V_{min}$. However, because the amount of change of the magnetic flux vector due to the lowering of the magnetic permeability of the temperature-sensitive magnetic substance 1, that is, the amount of change of the voltage value of the pickup coil 3 is always constant (if the relative positions and postures of the driving coil 2, the pickup coil 3, and other materials are fixed), it can be detected that the temperature of the portion to be measured reaches the target temperature from the amount of change of the voltage value of the pickup coil 3.

<Temperature Controlling Method>

A temperature controlling method of the present invention using the temperature measuring method of the present invention will be described below with reference to the drawing.

Figure 6:
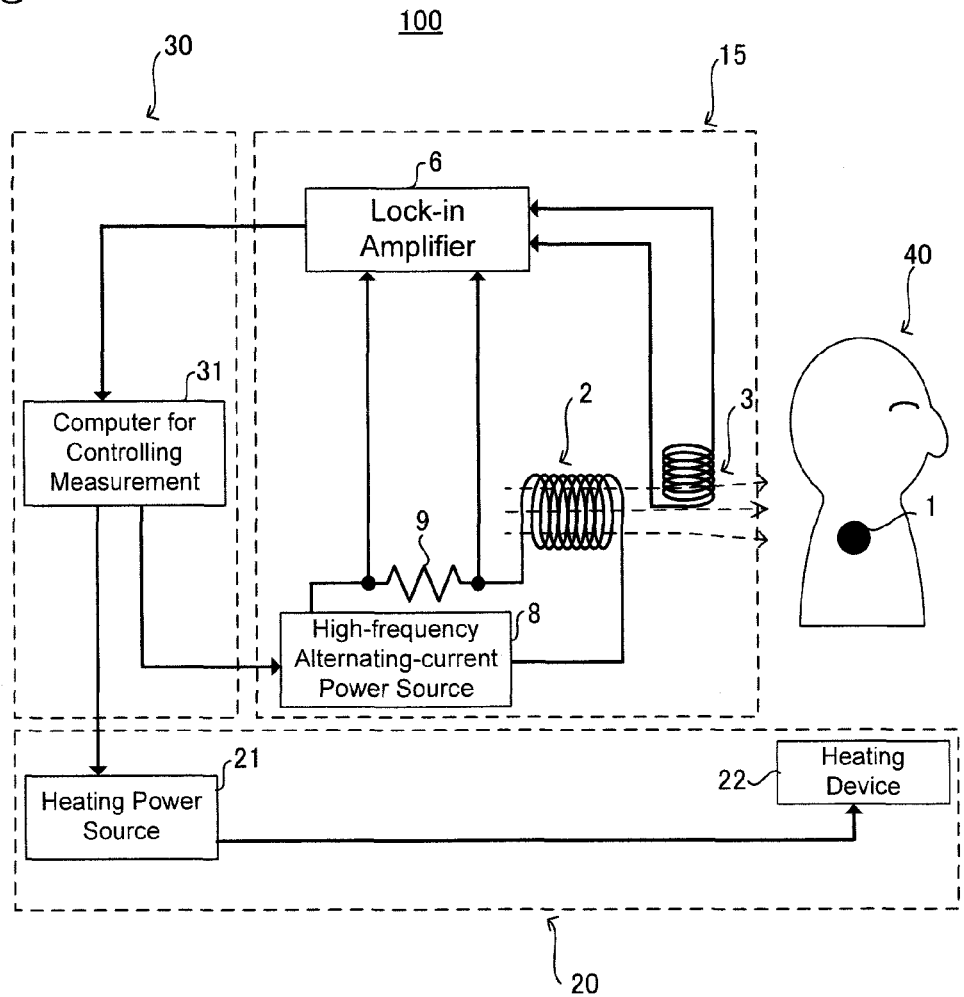
FIG. 6 is a diagram schematically showing an example of a temperature controlling system of the invention.

FIG. 6 is a diagram schematically showing an example of a temperature controlling system of the present invention. In FIG. 6, parts having the same configuration as FIGS. 1A to 4 are indicated by the same reference numerals as those used in FIGS. 1A to 4.

As shown in FIG. 6, a temperature controlling system 100 of the invention has the temperature-sensitive magnetic substance 1, the driving coil 2, the pickup coil 3, a high-frequency alternating-current power source 8 which supplies electricity to the driving coil 2, a detecting portion 15 having the lock-in amplifier 6 which synchronously detects the output from the pickup coil 3 according to the reference signal from the high-frequency alternating-current power source 8, a heating device 22 which heats the portion to be measured, a heating portion 20 having a heating power source 21 which supplies electricity to the heating device 22, and a controlling portion 30 having a computer 31 for controlling measurement which controls the high-frequency alternating-current power source 8 and the heating power source 21 according to the detection signal obtained from the detecting portion 15.

When an alternating current flows from the high-frequency alternating-current power source 8 to the driving coil 2, an alternating-current magnetic field is generated from the driving coil 2. The alternating-current magnetic field is affected by the magnetic properties of the temperature-sensitive magnetic substance 1 located at an arbitrary distance from the driving coil 2. The magnetic properties of the temperature-sensitive magnetic substance 1 depend on the temperature of the temperature-sensitive magnetic substance 1, so that the alternating-current magnetic field generated by the driving coil 2 is affected by the temperature of the temperature-sensitive magnetic substance 1. In other words, when the temperature of the temperature-sensitive magnetic substance 1 is less than the Curie point, the magnetic flux vector of the alternating-current magnetic field generated by the driving coil 2 is bent; when the temperature of the temperature-sensitive magnetic substance 1 is the Curie point or more, the magnetic flux vector of the alternating-current magnetic field generated by the driving coil 2 travels in a substantially straight line between the driving coil 2 and the temperature-sensitive magnetic substance 1.

As described above, when the magnetic flux vector of an alternating-current magnetic field generated by the driving coil 2 is bent, an induced electromotive force is generated in the pickup coil 3; meanwhile when the magnetic flux vector and the axis of the pickup coil 3 are substantially orthogonal to each other, an induced electromotive force generated in the pickup coil 3 is reduced as compared with the case where the magnetic flux vector is bent. That is, when the temperature of the temperature-sensitive magnetic substance 1 is the Curie point or more, an induced electromotive force generated in the pickup coil 3 is reduced as compared with the case where the temperature of the temperature-sensitive magnetic substance 1 is less than the Curie point. Therefore, by detecting an induced electromotive force generated in the pickup coil 3 disposed between the driving coil 2 and the temperature-sensitive magnetic substance 1, it is possible to make sure whether or not the temperature of the portion to be measured reaches the target temperature (i.e. the arbitrarily set Curie point of the temperature-sensitive magnetic substance). However, when the driving coil 2 and the temperature-sensitive magnetic substance 1 are spaced from each other, the amount of change of the magnetic flux vector is reduced, so that an induced electromotive force generated in the pickup coil 3 is hard to be detected. Consequently, in the temperature controlling system 100, electric signals (reference signals) taken from the positions sandwiching a resistor 9 between the high-frequency alternating-current power source 8 and the driving coil 2 are input to the lock-in amplifier 6, and an induced electromotive force generated in the pickup coil 3 is synchronously detected by the lock-in amplifier 6, to reduce magnetic field noise in the periphery and improve the detection sensitivity.

The detection signal obtained from the lock-in amplifier 6 is transmitted to the computer for controlling measurement 31, then the computer for controlling measurement 31 controls the high-frequency alternating-current power source 8 and the heating power source 21 according to the detection signal. Its specific example will be described below.

Figure 7:
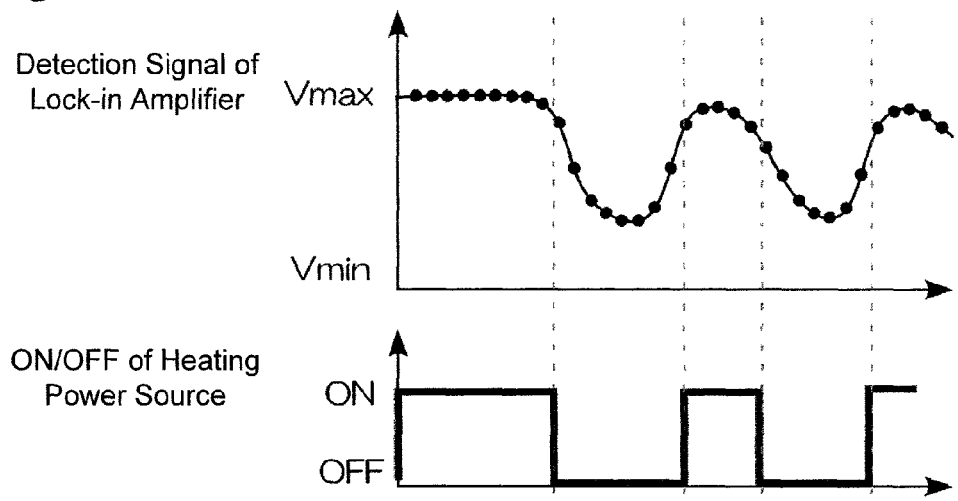
FIG. 7 is a diagram schematically showing an example of a time chart of a heating power source when operating the temperature controlling system of the invention.

FIG. 7 is a diagram schematically showing an example of a time chart of the heating power source 21 when operating the temperature controlling system of the present invention. The upper part of FIG. 7 shows the detection signal of the lock-in amplifier 6, the vertical axis shows signal intensity, and the meaning of $V_{max}$ and $V_{min}$ is as described above. The lower part shows the time chart of the heating power source 21. The horizontal axis shows time.

When the heating power source 21 is turned ON to continue to heat the portion to be measured by the heating device 22, the temperature of the portion to be measured is close to the target temperature (the Curie point of the temperature-sensitive magnetic substance 1), and the detection signal of the lock-in amplifier 6 is close to $V_{min}$. Thereafter, when the heating power source 21 is turned OFF to stop heating the portion to be measured, the temperature of the portion to be measured starts to be lowered, and after a while, the detection signal of the lock-in amplifier 6 starts to be close to $V_{max}$. Thereafter, when the heating power source 21 is turned ON again to heat the portion to be measured, the detection signal of the lock-in amplifier 6 starts to be close to $V_{min}$. In this manner, by repeatedly turning the heating power source 21 ON and OFF, it is possible to control the temperature of the portion to be measured to be constant.

In the embodiment shown in FIG. 6, the heating power source 21 and the heating device 22 are used as a heating portion. When the temperature-sensitive magnetic substance 1 or a mixture of the temperature-sensitive magnetic substance 1 and the exothermic material which is easily inductively heated are used can be inductively heated, the driving coil 2 can also serve as the heating portion. In other words, the temperature-sensitive magnetic substance 1 or the mixture is inductively heated using a magnetic field generated by the driving coil 2, the temperature-sensitive magnetic substance 1 or the mixture as a heat source heats the portion to be measured, and the heating amount can be adjusted. In this case, the use of the mixture of the temperature-sensitive magnetic substance 1 and the exothermic material which is easily inductively heated can heat the portion to be measured more easily, thereby it is preferable. According to such a method, thermotherapy can be performed without using any heating electrodes.

Figure 8:
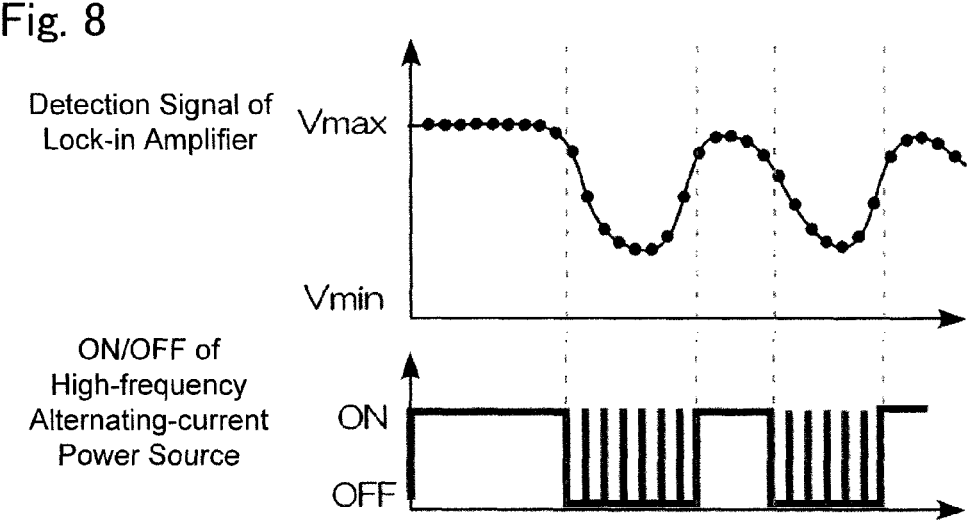
FIG. 8 is a diagram schematically showing an example of a time chart of a high-frequency alternating-current power source when operating the temperature controlling system of the invention.

A method of controlling the temperature of the portion to be measured while heating the temperature-sensitive magnetic substance 1 using the driving coil 2 will be described below with reference to FIG. 8. FIG. 8 is a diagram schematically showing an example of a time chart of the high-frequency alternating-current power source 8 which supplies electricity to the driving coil 2 when operating the temperature controlling system of the present invention. The upper part of FIG. 8 shows the detection signal of the lock-in amplifier 6, the vertical axis shows signal intensity, and the meaning of $V_{max}$ and $V_{min}$ is as described above. The lower part shows the time chart of the high-frequency alternating-current power source 8. The horizontal axis shows time.

When the high-frequency alternating-current power source 8 is turned ON to continue to inductively heat the temperature-sensitive magnetic substance 1 by a magnetic field generated by the driving coil 2, the temperature of the temperature-sensitive magnetic substance 1 becomes closer to the target temperature (i.e. the Curie point of the temperature-sensitive magnetic substance 1), and the detection signal of the lock-in amplifier 6 becomes closer to $V_{min}$. Thereafter, when the high-frequency alternating-current power source 8 is turned OFF to stop heating the portion to be measured, the temperature of the portion to be measured starts to be lowered, and after a while, the detection signal of the lock-in amplifier 6 starts to be closer to $V_{max}$. At this time, while the high-frequency alternating-current power source 8 is OFF, no electricity can be supplied to the driving coil 2. Therefore, the detection signal of the lock-in amplifier 6 (the pickup coil 3) cannot be obtained. The high-frequency alternating-current power source 8 is intermittently turned ON to discretely obtain the detection signal (temperature information). In this way, the high-frequency alternating-current power source 8 is always turned ON at the time of heating the temperature-sensitive magnetic substance 1 and the high-frequency alternating-current power source 8 is intermittently turned ON at the time of holding temperature, the detection signal (temperature information) can be discretely obtained and the temperature of the portion to be measured can be controlled.

In the above description of the present invention, the form of using the coil as the magnetic field generation source and the magnetic sensor has been described. The present invention is not limited to such a form. In the temperature measuring method of the present invention, as long as a magnetic field is generated from the magnetic field generation source and the change of the magnetic flux vector of the magnetic field changed upon reception of the influence of the magnetic properties of the temperature-sensitive magnetic substance depending on temperature is detected, it is preferable. Specific examples of the magnetic field generation source usable in the present invention can include, other than the coil, a superconductive coil and a permanent magnet. Specific examples of the magnetic sensor can include, other than a coil, a hall device, a magnetoresistance effect device, a flux gate sensor, a Faraday element, and a superconductive quantum interference device. From the viewpoint of the improvement of the durability of the system, the reduction of the cost, and the removal of a cross-axis effect caused in a semiconductor device, the coil is preferably used as the magnetic field generation source and the magnetic sensor.

EXAMPLES

The present invention will be described below more with reference to the examples.

To study the validity of the temperature measuring method of the present invention, the measuring unit 10 and the temperature-sensitive magnetic substance were used to perform various examinations. The following examinations were performed by flowing an alternating current of 640 Hz and 10 Ap-p to the driving coil 2. The temperature-sensitive magnetic substance including $Fe_2O_3$, $CuO$, $ZnO$, and $MgO$ was used. Unless otherwise specified, the temperature-sensitive magnetic substance in which the Curie point was set to 43° C. (the composition ratio [mol %] is $Fe_2O_3$:$CuO$:$ZnO$:$MgO$=49:7:30:14) was used.

<The Relation Between the Temperature of the Temperature-sensitive Magnetic Substance and the Output Voltage of the Detecting Device at an Arbitrary Distance>

The spherical temperature-sensitive magnetic substance having a diameter of 2 cm was put into water in a water tank to dispose the pickup coil 3 at an arbitrary distance (2 cm, 2.5 cm) from the temperature-sensitive magnetic substance. The change of the magnetic flux vector of an alternating-current magnetic field generated from the driving coil 2 when a water temperature in the water tank into which the temperature-sensitive magnetic substance was put (hereinafter, simply called a "water temperature".) was changed was examined. In this examination, assuming therapy in a body in thermotherapy, the water temperature was continuously changed from 32° C. to 45° C. to examine the relation between the water temperature and the output voltage detected by the lock-in amplifier 6 (hereinafter, simply called an "output voltage".).

Figure 9:
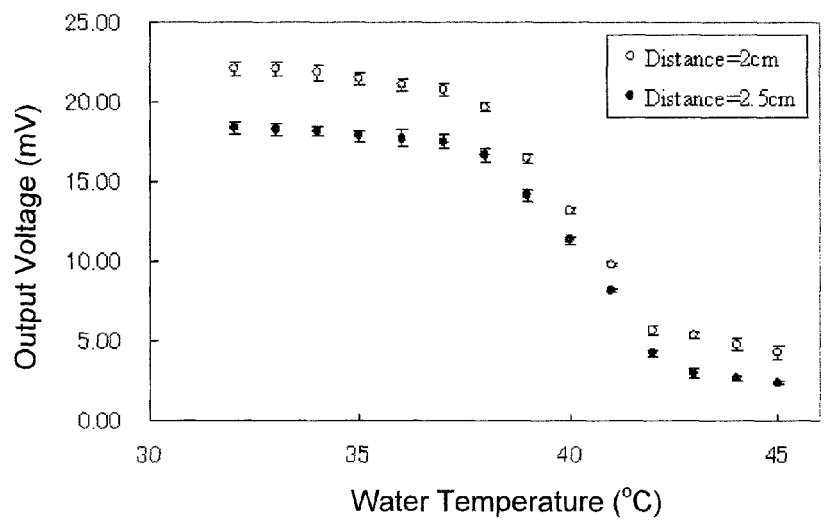
FIG. 9 is a diagram showing the relation between water temperature and output voltage at arbitrary distances.

FIG. 9 shows the relation between water temperature and output voltage. The "d=" in the drawing means the distance between the temperature-sensitive magnetic substance and the pickup coil 3. The horizontal axis shows the water temperature (the temperature in the periphery of the temperature-sensitive magnetic substance), and the vertical axis shows the output voltage. From FIG. 9, it is found that the output voltage is largely changed before and after the Curie point (43° C.) of the temperature-sensitive magnetic substance. According to the temperature measuring method of the present invention, by detecting the amount of change of the magnetic flux vector, it is found in a non-contact manner that whether or not the temperature of the portion to be measured reaches the arbitrary temperature (the Curie point of the temperature-sensitive magnetic substance) can be determined.

Next, the distance between the pickup coil 3 and the temperature-sensitive magnetic substance was set to 1 cm, 2 cm, 3 cm, 4 cm, 5 cm, 6 cm, and 7 cm to examine the relation between the water temperature and the output voltage in the case of respective distance when the water temperature in the water tank is 37° C., 40° C., 43° C., and 46° C.

Figure 10:
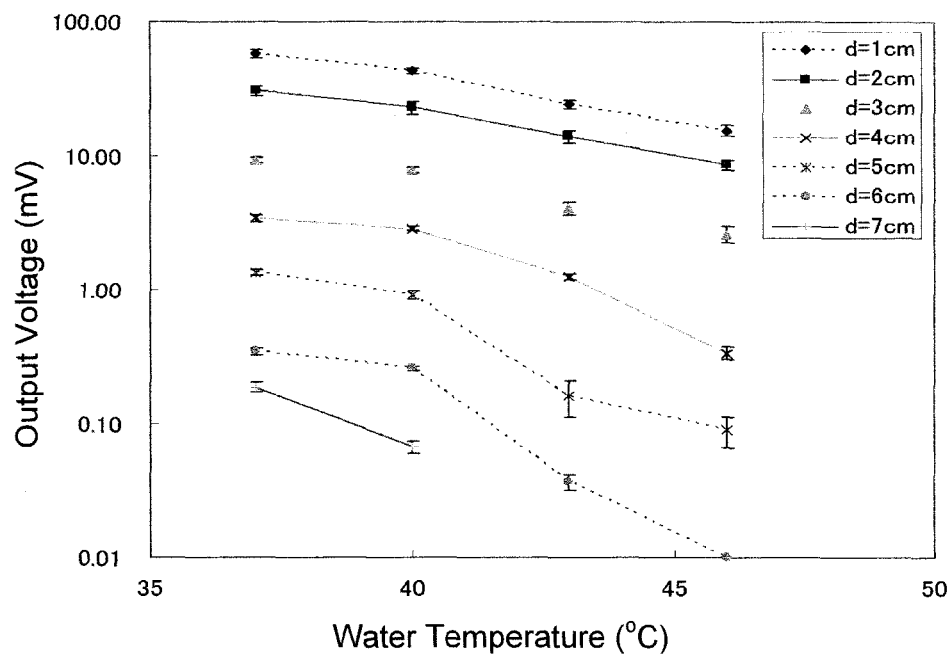
FIG. 10 is a diagram showing the relation between water temperature and output voltage at arbitrary distances.

FIG. 10 shows the relation between water temperature and output voltage when the pickup coil 3 is placed at an arbitrary distance (1 cm, 2 cm, 3 cm, 4 cm, 5 cm, 6 cm, and 7 cm) from the temperature-sensitive magnetic substance in the water tank. The "d=" in the drawing means the distance between the temperature-sensitive magnetic substance and the pickup coil 3. The horizontal axis shows the water temperature (i.e. the temperature in the periphery of the temperature-sensitive magnetic substance), and the vertical axis shows the output voltage. When examining the output voltage when the distance between the temperature-sensitive magnetic substance and the pickup coil 3 was 6 cm, a difference of −15 dB was obtained before and after the Curie point under the conditions of this experiment. Even when the distance between the temperature-sensitive magnetic substance and the pickup coil 3 was 6 cm, it was found that measurement was sufficiently enabled.

To detect the change of the temperature (magnetic permeability) of the temperature-sensitive magnetic substance at a further position, it is considered that the magnetic flux density of the driving coil 2, the inductance of the pickup coil 3, or the inner diameter of the driving coil 2 is increased.

<The Relation Between the Temperature of the Temperature-sensitive Magnetic Particulates in a Phantom and the Output Voltage>

The temperature-sensitive magnetic substance particulates having a weight of 1 g and a particle diameter of 50 to 150 μm are buried into a dummy living body (phantom) to measure the temperature of the center portion of the temperature-sensitive magnetic substance particulates by an optical fiber temperature gage.

Figure 11:
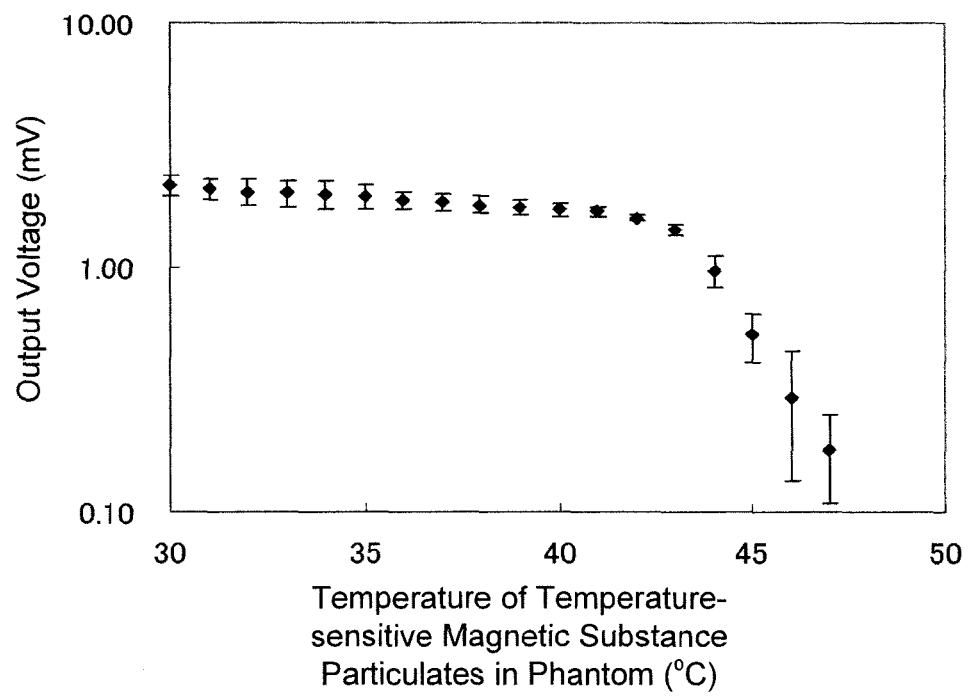
FIG. 11 is a diagram showing the relation between the temperature of temperature-sensitive magnetic substance particulates in a phantom (i.e. a dummy living body) and output voltage.

FIG. 11 shows the relation between the temperature of the temperature-sensitive magnetic substance particulates injected into the phantom and the output voltage. As shown in FIG. 11, the temperature of the temperature-sensitive magnetic substance particulates was abruptly lowered near the Curie point. It is considered that in the particulates state, the thermal capacity is lowered due to the reduced size, which can follow the abrupt temperature change. Accordingly, it is found that the temperature near the Curie point can be detected at high sensitivity by using the temperature-sensitive magnetic substance particulates.

<Continuous Temperature Measurement>

A plurality of temperature-sensitive magnetic substances having different Curie points were used all together to perform continuous temperature measurement. Here, a phantom in which 1 g of a temperature-sensitive magnetic substance particulates having the Curie point of 43° C. and 1 g of temperature-sensitive magnetic substance particulates having the Curie point of 48° C. were mixed was an object to measure the change of magnetic flux vector.

Figure 12:
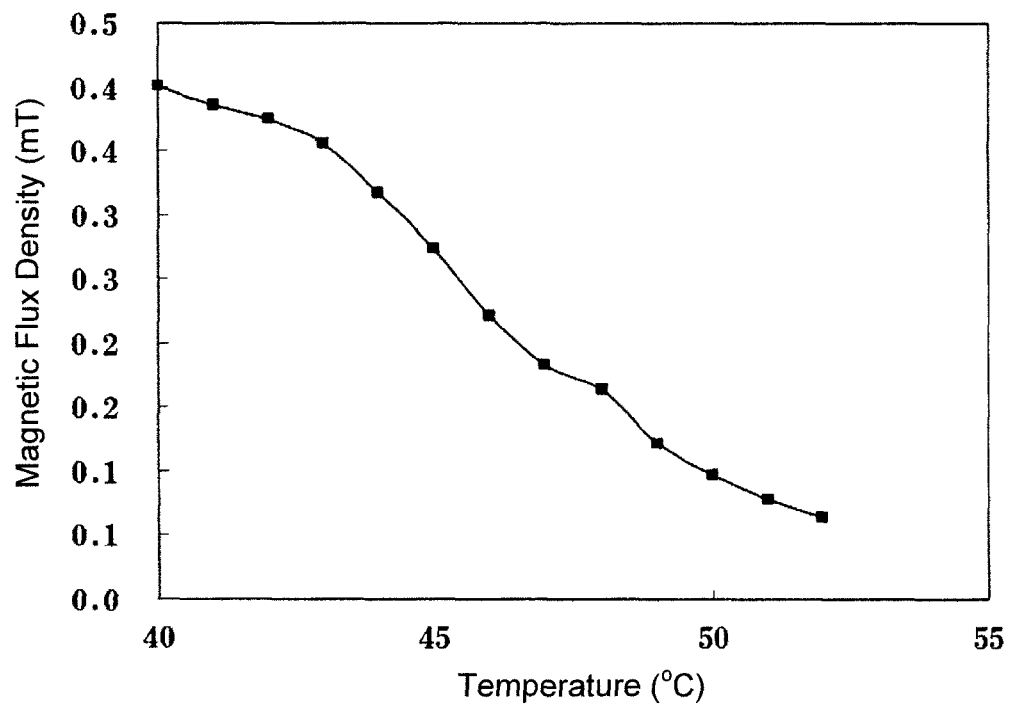
FIG. 12 is a diagram showing the measurement result of magnetic flux vector when using a plurality of temperature-sensitive magnetic substances respectively having different Curie points all together.

In FIG. 12, the horizontal axis shows the temperature of the portion to be measured, and the vertical axis shows the magnetic flux density. The magnetic flux density is converted according to an experiment equation using that the output voltage and the magnetic flux density are proportional. From FIG. 12, the large reduction of the magnetic flux vector is seen at 43° C. and 48° C. as the Curie points. It can be found that the magnetic flux density is reduced substantially linearly in the range from 43° C. to 52° C. and the temperature and the magnetic flux vector are proportional. From this result, it is found that continuous temperature measurement can be attained by a combination of a plurality of the temperature-sensitive magnetic substances respectively having different Curie points.

The above has described the present invention associated with the most practical and preferred embodiments thereof. However, the invention is not limited to the embodiments disclosed in the specification. Thus, the invention can be appropriately varied as long as the variation is not contrary to the subject substance and conception of the invention which can be read out from the claims and the whole contents of the specification. It should be understood that the temperature measuring method, the temperature controlling method, and the system for use in those methods with such an alternation are included in the technical scope of the invention.

The invention claimed is:

1. A temperature measuring method comprising the steps of:
arranging in a portion to be measured a temperature-sensitive magnetic substance having an arbitrary Curie point;
generating a magnetic field from a magnetic field generation source disposed at a position away from the portion to be measured; and
detecting a change of the magnetic flux vector of the magnetic field depending on the temperature of the temperature-sensitive magnetic substance by a magnetic sensor disposed between the temperature-sensitive magnetic substance and the magnetic field generation source, whereby the temperature of the portion to be measured is measured.

2. A temperature measuring method comprising the steps of:
arranging in a portion to be measured a plurality of temperature-sensitive magnetic substances respectively having arbitrary different Curie points;
generating a magnetic field from a magnetic field generation source disposed at a position away from the portion to be measured; and
detecting a change of the magnetic flux vector of the magnetic field depending on the temperature of the temperature-sensitive magnetic substance by a magnetic sensor disposed between the temperature-sensitive magnetic substance and the magnetic field generation source, whereby the temperature of the portion to be measured is measured.

3. The temperature measuring method according to claim 1, wherein the magnetic field generation source is a coil which flows an alternating current.

4. The temperature measuring method according to claim 1, wherein the magnetic sensor is a coil.

5. The temperature measuring method according to claim 1, wherein the temperature-sensitive magnetic substance is particulate.

6. The temperature measuring method according to claim 1, wherein the temperature-sensitive magnetic substance is used together with an exothermic material which is easily inductively heated.

7. The temperature measuring method according to claim 1,
wherein the relative positions and postures of the magnetic sensor and the magnetic field generation source are adjusted and fixed so that the output of the magnetic sensor is a minimum value ($V_{min}$),
wherein the temperature-sensitive magnetic substance is arranged in the portion to be measured, and the relative positions and postures of the magnetic sensor, the magnetic field generation source, and the temperature-sensitive magnetic substance are adjusted and fixed so that the output of the magnetic sensor is a maximum value ($V_{max}$),
wherein the output (V) of the magnetic sensor when the temperature of the portion to be measured reaches a target temperature is calculated from the following calculation equation:

calculation equation: $V=(V_{max}-V_{min}) \times k + V_{min}$
(wherein, $k$ is a constant of $0<k<1$).

8. A temperature measuring system comprising:
a temperature-sensitive magnetic substance arranged in a portion to be measured and having an arbitrary Curie point; and
a detecting portion which generates a magnetic field in a position away from the portion to be measured and detects a change of the magnetic flux vector of the magnetic field depending on the temperature of the temperature-sensitive magnetic substance.

9. The temperature measuring system according to claim 8, wherein the detecting portion has a magnetic field generation source which generates a magnetic field in a position away from the portion to be measured, and a magnetic sensor which detects a change of the magnetic flux vector of the magnetic field depending on the temperature of the temperature-sensitive magnetic substance.

10. The temperature measuring system according to claim 9, wherein the detecting portion further comprises a lock-in amplifier.

11. A temperature controlling method comprising the steps of:
arranging in a portion to be measured a temperature-sensitive magnetic substance having an arbitrary Curie point;
heating the portion to be measured by a heating device;
generating a magnetic field from a magnetic field generation source disposed at a position away from the portion to be measured;
detecting a change of the magnetic flux vector of the magnetic field depending on the temperature of the temperature-sensitive magnetic substance by a magnetic sensor; and
controlling the heating device according to a detection signal from the magnetic sensor.

12. The temperature controlling method according to claim 11, wherein the magnetic field generation source also serves as a heating device.

13. A temperature controlling system comprising:
a temperature-sensitive magnetic substance arranged in a portion to be measured and having an arbitrary Curie point;
a detecting portion which generates a magnetic field in a position away from the portion to be measured and detects a change of the magnetic flux vector of the magnetic field depending on the temperature of the temperature-sensitive magnetic substance;
a heating portion which heats the portion to be measured; and
a controlling portion having a computer which controls the heating portion according to a detection signal obtained from the detecting portion.

14. The temperature controlling system according to claim 13,
wherein the detecting portion has a magnetic field generation source which generates a magnetic field in a position away from the portion to be measured and the magnetic field generation source serves as the heating portion by inductively heating the temperature-sensitive magnetic substance.

15. A temperature measuring method comprising:
generating a magnetic field from a magnetic field generation source; and detecting a change of the magnetic flux by a magnetic sensor,
wherein a temperature-sensitive magnetic substances having arbitrary different Curie points is arranged in a portion to be measured in a form which does not prevent the magnetic sensor from detecting the magnetic flux vector, and a change of the magnetic flux vector depending on the temperature of the temperature-sensitive magnetic substance is detected, whereby the temperature of the portion to be measured is measured.

16. The temperature measuring method according to claim 2, wherein the magnetic field generation source is a coil which flows an alternating current.

* * * * *